United States Patent [19]
Trantow

[11] Patent Number: 5,974,889
[45] Date of Patent: Nov. 2, 1999

[54] ULTRASONIC MULTI-TRANSDUCER ROTATABLE SCANNING APPARATUS AND METHOD OF USE THEREOF

[75] Inventor: Richard L. Trantow, Cincinnati, Ohio

[73] Assignee: General Electric Company, Cincinnati, Ohio

[21] Appl. No.: 09/002,355

[22] Filed: Jan. 2, 1998

[51] Int. Cl.$^6$ .......................... G01N 29/10; G01N 29/24
[52] U.S. Cl. ................. 73/624; 73/625; 73/628; 73/633
[58] Field of Search ................. 73/597, 599, 602, 73/620, 621, 622, 624, 625, 627, 628, 632, 633, 634

[56] References Cited

U.S. PATENT DOCUMENTS

| | | | |
|---|---|---|---|
| 2,799,157 | 7/1957 | Pohlman | 73/635 |
| 2,995,925 | 8/1961 | Worlton | 73/627 |
| 3,340,953 | 9/1967 | Zemanek, Jr. | 367/28 |
| 3,512,400 | 5/1970 | Lynnworth | 73/597 |
| 3,580,057 | 5/1971 | Seegmiller | 73/597 |
| 3,676,584 | 7/1992 | Plakas et al. | 73/614 |
| 3,937,067 | 2/1976 | Flambard et al. | 73/627 |
| 4,098,129 | 7/1978 | Deblaere et al. | 73/599 |
| 4,210,028 | 7/1980 | Hildebrand | 73/598 |
| 4,338,820 | 7/1982 | Jassby et al. | 73/597 |
| 4,435,985 | 3/1984 | Wickramasinghe | 73/642 |
| 4,462,256 | 7/1984 | Moffett | 73/642 |
| 4,524,621 | 6/1985 | Yamanaka | 73/597 |
| 4,574,637 | 3/1986 | Adler et al. | 73/629 |
| 4,606,235 | 8/1986 | Kindt | 74/113 |
| 4,718,277 | 1/1988 | Glascock | 73/622 |
| 4,765,196 | 8/1988 | Russ | 74/436 |
| 4,817,016 | 3/1989 | Thompson et al. | 73/598 |
| 5,024,093 | 6/1991 | Sasaki et al. | 73/633 |
| 5,111,696 | 5/1992 | Lund et al. | 73/627 |
| 5,421,200 | 6/1995 | Casarcia et al. | 73/632 |
| 5,447,070 | 9/1995 | Patzke et al. | 73/621 |
| 5,481,945 | 1/1996 | Whipple et al. | 74/820 |
| 5,485,751 | 1/1996 | Karbach et al. | 73/618 |

OTHER PUBLICATIONS

"Measurement of Applied and Residual Stresses Using an Ultrasonic Instrumentation System", by B.E. Gordon, Jr., ISA Transactions, vol. 19, No. 2, pp. 33–41.

"Acoustic Evaluation Of Cold Work In 316 Stainless Steel Tubing And Plate", by R.L. Trantow, Prepared for the U.S. Atomic Energy Commission Division of Reactor Development and Technology, Jun., 1973.

*Primary Examiner*—Hezron Williams
*Assistant Examiner*—Rose M. Miller
*Attorney, Agent, or Firm*—Andrew C. Hess; Gerry S. Gressel

[57] ABSTRACT

An apparatus for ultrasonically scanning a surface includes a plurality of pairs of 180 degree oppositely disposed transducers mounted in a rotatable head having a central axis about which the head is rotatable. A positioning system for positioning the transducers such that all beam axes of the transducers intersect the central axis at a single point. Axes of each pair are equiangular with respect to the centerline and axes of different pairs have incident and reflective angles between beam axes and the central axis that are different from those of other pairs. Incident and reflective angles of different pairs of transducers are preferably predetermined and in close proximity to a predetermined angle over a range of angles bracketing a predetermined critical angle. A translating system is preferably included for effecting translational motion between the head and the surface such that the single point lies substantially on the surface during scanning. The present method further provides a non-destructive material evaluation technique to determine effective Rayleigh wave critical angles using the apparatus. The effective critical angle may be determined from an angular beam intensity profile generated from the beam intensity data provided by each pair of fixed angle transducers.

23 Claims, 3 Drawing Sheets

ULTRASONIC MULTI-TRANSDUCER ROTATABLE SCANNING APPARATUS AND METHOD OF USE THEREOF

This patent is related to U.S. application Ser. No. 09/002,499, still pending, filed Jan. 2, 1998.

BACKGROUND OF THE INVENTION

1. Field of the Invention

The present invention generally relates to an apparatus for non-destructive testing of material using ultrasonic waves and, in particular, an apparatus having multiple pairs of 180 degree spaced apart pitch and catch transducers. Each pair has a different central angle between them and are mounted on a rotatable head of the apparatus such that the apparatus may be used for determining Rayleigh wave or Stonely wave critical angles for purposes such as validation of laser shock peening of metallic materials or measurement of the magnitude of the laser shock peening effect.

2. Discussion of the Background Art

Laser shock peening or laser shock processing, as it also referred to, is a process for producing a region of deep compressive residual stresses imparted by laser shock peening portions of a surface area of a workpiece. Laser shock peening typically uses multiple radiation pulses from high power pulsed lasers to produce shock waves on the surface of a workpiece similar to methods disclosed in U.S. Pat. No. 3,850,698, entitled "Altering Material Properties"; U.S. Pat. No. 4,401,477, entitled "Laser Shock Processing"; and U.S. Pat. No. 5,131,957, entitled "Material Properties". Laser peening as understood in the art and as used herein utilizes a laser beam to produce a strong localized compressive force on a portion of a surface by producing an explosive force. The explosive force is produced by instantaneous ablation or vaporization of a painted or coated or uncoated surface beneath a force containing overlay which is typically a water curtain. Laser peening has been utilized to create a compressively stressed protection layer at the outer surface of a workpiece which is known to considerably increase the resistance of the workpiece to fatigue failure as disclosed in U.S. Pat. No. 4,937,421, entitled "Laser Peening System and Method". Many methods and uses for using laser shock peening have been developed and could benefit from an accurate method of validation and non-destructive testing of the effects of the process.

Material property inspection and evaluation using beams of ultrasonic waves reflected from the surface of materials are known to yield valuable information about mechanical properties of the surface layers of the materials such as variations in Young's modulus induced by thermal treatment of the material as disclosed in U.S. Pat. No. 4,098,129. Known methods include directing a beam of ultrasonic waves onto the surface of the material at a variable angle of incidence, detecting the energy of the corresponding reflected beam, and determining the critical angle of incidence at which the energy (or the amplitude of the reflected waves) appear to pass through a minimum. At the critical angle the acoustic energy within the material propagates along the surface of the material in what are defined as Rayleigh or Stonely waves which decrease logarithmically in amplitude with depth. Together with couplant velocities and Snell's Law, the critical angle can be used to calculate the propagation speed of the Rayleigh ultrasonic waves at the surface of the material. It is well known that the surface wave velocities indicated by these critical angles are useful in comparing material properties and changes in these properties. Non-destructive evaluation means and methods of flaw reconstruction utilizing an ultrasonic multi-viewing transducer data acquisition system are disclosed in U.S. Pat. No. 4,817,016.

An article in the ISA Transactions, Vol. 19, No. 2, published in 1980, entitled "Measurement of Applied and Residual Stresses" discloses an ultrasonic instrumentation system developed for nondestructive measurements of applied and residual stresses. The article discloses a system that measures time of flight of an ultrasonic wave through a material with a resolution of 0.1 nanoseconds and discusses how time of flight correlates directly with elastic stress levels. U.S. Pat. No. 4,210,028, entitled "Method And Apparatus For Ultrasonically Measuring Concentrations Of Stress", discloses an apparatus and method for ultrasonically measuring concentrations of stress in objects of interest. The apparatus includes an ultrasonic transducer array for propagating acoustic waves in the object along a plurality of determinable directions and from a plurality of determinable positions. Time of flight measurements are made and reconstructed into a map of the variations in acoustic velocity within the object. The changes in acoustic velocity are then mathematically converted into a map of stress concentration areas in the object of interest.

It is believed that laser shock peening imparts increased resistance to crack initiation and propagation resulting from cyclic fatigue by producing compressive residual stresses in the laser shock peened material. In addition to the compressive residual stress, the material may also be strengthened by the local work hardening due to plastic deformation at the site of the laser shock. Also, the orientation and degree of preferential crystallographic texture are expected to affect the fatigue damage tolerance of the part. All of these structural conditions affect the velocity of the different modes of acoustic wave propagation within a material. The wave propagation mode employed in this methodology is referred to as a Rayleigh wave, or Stonely wave. These are surface waves that decrease exponentially in amplitude with depth into the material. The velocity sensing methodology described in this disclosure employs Rayleigh waves generated by refraction, and senses their presence by a decrease, or "null" in the amplitude of the ultrasonic beam that is both reflected and re-radiated from the part's surface. It is well recognized that the Rayleigh or critical angle at the null may be used to determine and analyze absolute and relative material properties for evaluation and comparative purposes.

The Rayleigh wave may be generated by refraction of the incident acoustic beam at a liquid solid interface where the liquid, often water, is referred to as a couplant. The angle at which an incident longitudinal or compressional wave is refracted and converted to a Rayleigh wave propagating parallel with the surface of the material is referred to as the Rayleigh Critical Angle. Changes in the Rayleigh Critical Angle at which these surface waves are generated are an indicator of changes in the Rayleigh wave velocity and, therefore, an indicator of changes in material properties.

It has been found that the angle at which the Rayleigh Wave is generated is evidenced by a "sharp" decrease, or "null" in the intensity profile of the superimposed reflected and re-radiated acoustic beam. The depth of the null has been found to be a function of the attenuation within the material and of the wave length or frequency of the acoustic beam. There is a frequency related maximum null condition, and there is also a phase change associated with the received signal that is dependent on whether the frequency of the incident beam is above or below that associated with the maximum null. Because of these effects, simply measuring the changes in the amplitude of the received signal at some single fixed angle slightly smaller or larger than the Rayleigh Critical Angle (on the slope of the null) will result in indications colored by the effects of many material properties such as grain size, preferential crystallographic orientation or texture, work hardening, etc. and measurement related variables such as couplant temperature. To separate the effects of attenuation from properties related to residual stress and texture some means of directly determining the angular position of the null must be employed in a quick and effective manner suitable for process validation in a production environment. U.S. Patent No. (GE DOCKET NO. 13DV-12450) is directed towards this purpose and is herein incorporated by reference. The apparatus and method of the present invention was developed to quickly and effectively ultrasonically scan a processed surface and employ the data analysis of the methods disclosed in (GE DOCKET NO. 13DV-12450).

SUMMARY OF THE INVENTION

An apparatus for ultrasonically scanning a surface includes a plurality of pairs of 180 degree oppositely disposed and mounted in a rotatable head having a central axis about which the head is rotatable. The ultrasonic transducers have axes of transmission or beam axes and the apparatus includes a positioning system for positioning the transducers such that all of the beam axes intersect the central axis at a single point, the beam axes of each pair of the transducers are equiangular with respect to the central axis, and the beam axes of different pairs of transducers are different with respect to the central axis from other pairs of transducers. The positioning system may be a fixture having a plurality of angled holes in which the transducers are disposed. Distances from the transducers to the single point along the transmission axes may are preferably equal but not required to be so. Transducer angles between the beam axes and the central axis of different pairs of transducers are preferably predetermined and in close proximity to a predetermined angle and in one embodiment of the present invention the transducer angles are set at intervals of about 0.2 degrees over a range of angles bracketing the predetermined angle. The apparatus further may include a translating system for effecting translational motion between head and the surface and positioning the head with respect to the surface such that the single point lies substantially on the surface during ultrasonic scanning.

If the rotating head is to be stopped during each beam intensity measurement then it is preferable to further include a counter-rotatable annular collar encircling the head. The mass of the collar and its motion are selected to counterbalance the inertial effects of starting and stopping the head.

The present method further provides a non-destructive material evaluation technique using ultrasonic waves to determine effective Rayleigh wave critical angles associated with the Rayleigh surface wave velocity within an inspected area. This may particularly useful in quality control to evaluate the degree of change in properties due to materials processing operations such as laser shock peening. The effective Rayleigh wave critical angles of the present invention may not be exact but are sufficient for use in quality control to evaluate the degree of change in properties due to materials processing operations.

The Rayleigh critical angle is defined as the angle of incidence at which the intensity of the received acoustic beam is reduced to a minimum value at an angle associated with the Rayleigh wave and couplant velocities and Snell's Law. The effective critical angle may be determined from an angular beam intensity profile generated from the beam intensity data provided by each pair of fixed angle transducers. The angular location of the null is determined from the intensity profile by applying a curve fit, such as a second order polynomial curve fit, to a mid to lower intensity portion of the null profile, and determining the effective critical angle which is equal to the inflection point of the fit curve. Higher order polynomial or other curve fits may be employed.

Another embodiment provides mapping of Rayleigh wave effective critical angles over the surface area of an object by scanning a plurality of points on the area. The method includes scanning at a plurality of incident angles by rotating the plurality of pairs of 180 degree oppositely disposed ultrasonic transducers mounted in the rotatable head. The scanning may include a plurality of passes of the rotatable head with the transducers held at a fixed angular orientation around the central axis during each pass. The head is rotated between passes such that different ones of the plurality of transducers are used as pitch and catch transducers in each of the passes. Alternatively, the head may be rotated at each successive data acquisition point on the material surface so as to bring all transducer pairs of interest to the desired rotational orientation (relative to the part or scan direction) for acquisition before completing the move to the next successive data acquisition point. The pitch and catch transducers may be operated in bursts over the points in the area during each pass. A plurality of null angle profiles of data indicating intensity versus corresponding incident angles at the plurality of points on the area are used for determining intensity profiles for the points by applying a polynomial curve fits to the mid to lower intensity portions of the null angle profiles. The null angle inflection points, determined through these curve fits, may then be combined with the velocity of the couplant fluid and Snell's Law to determine the Rayleigh surface wave velocity.

ADVANTAGES

The present invention has many advantages over apparatus and methods in the art and, in particular, it offers a faster more accurate system of directing a beam of ultrasonic waves on to the surface of the material at different angles of incidence, detecting the energy of the corresponding reflected beams, and determining the critical angle of incidence at which the energy (or the amplitude of the reflected waves) passes through a minimum. The apparatus and method of the present invention is also advantageous because it is very quick and has a robust design that is easy to use on an assembly line or in a plant. It may be used to evaluate effects of many other material properties such as grain size, preferential crystallographic orientation or texture, work hardening, etc. and measurement related variables such as couplant temperature. Yet another advantage of the present invention is that it is quick and effective and, therefore, suitable for process validation in a production environment.

These features and advantages will become more readily apparent in the following description when taken in conjunction with the appended drawings.

BRIEF DESCRIPTION OF THE DRAWINGS

The invention, together with further objects and advantages thereof, is more particularly described in conjunction with the accompanying drawings in which.

DETAILED DESCRIPTION

Figure 1:
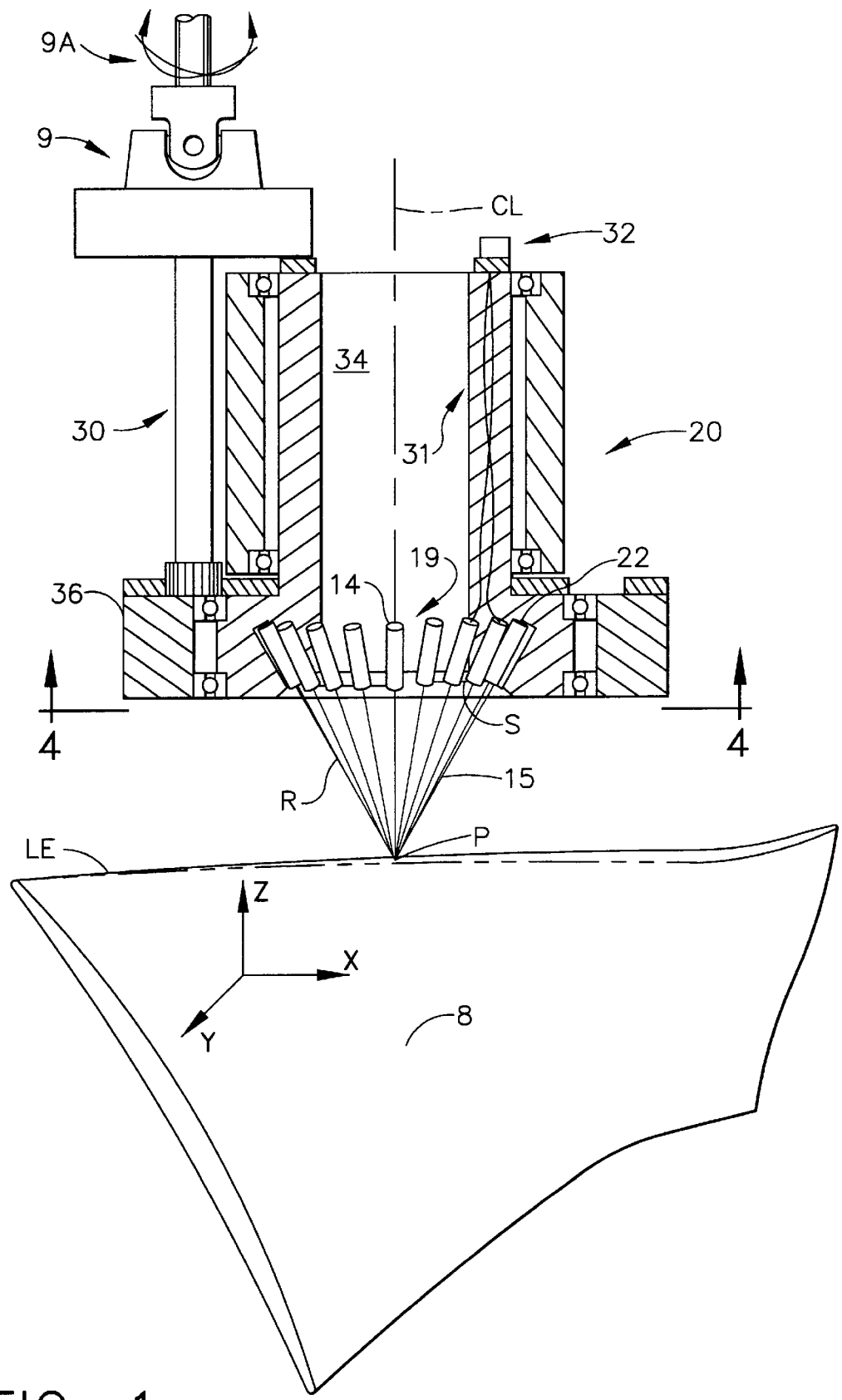
FIG. 1 is a partial perspective and partial cut away illustration of a scanning apparatus having a plurality of fixed angle ultrasonic transducers in accordance with an exemplary embodiment of the present invention.
Figure 2:
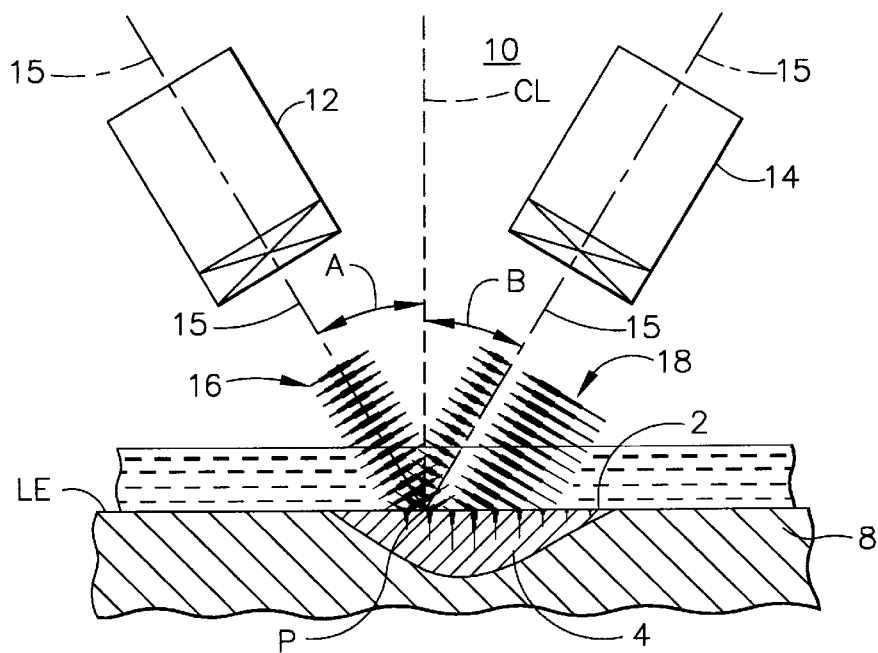
FIG. 2 is a general diagram of one pair of the transducers in FIG. 1.
Figure 4:
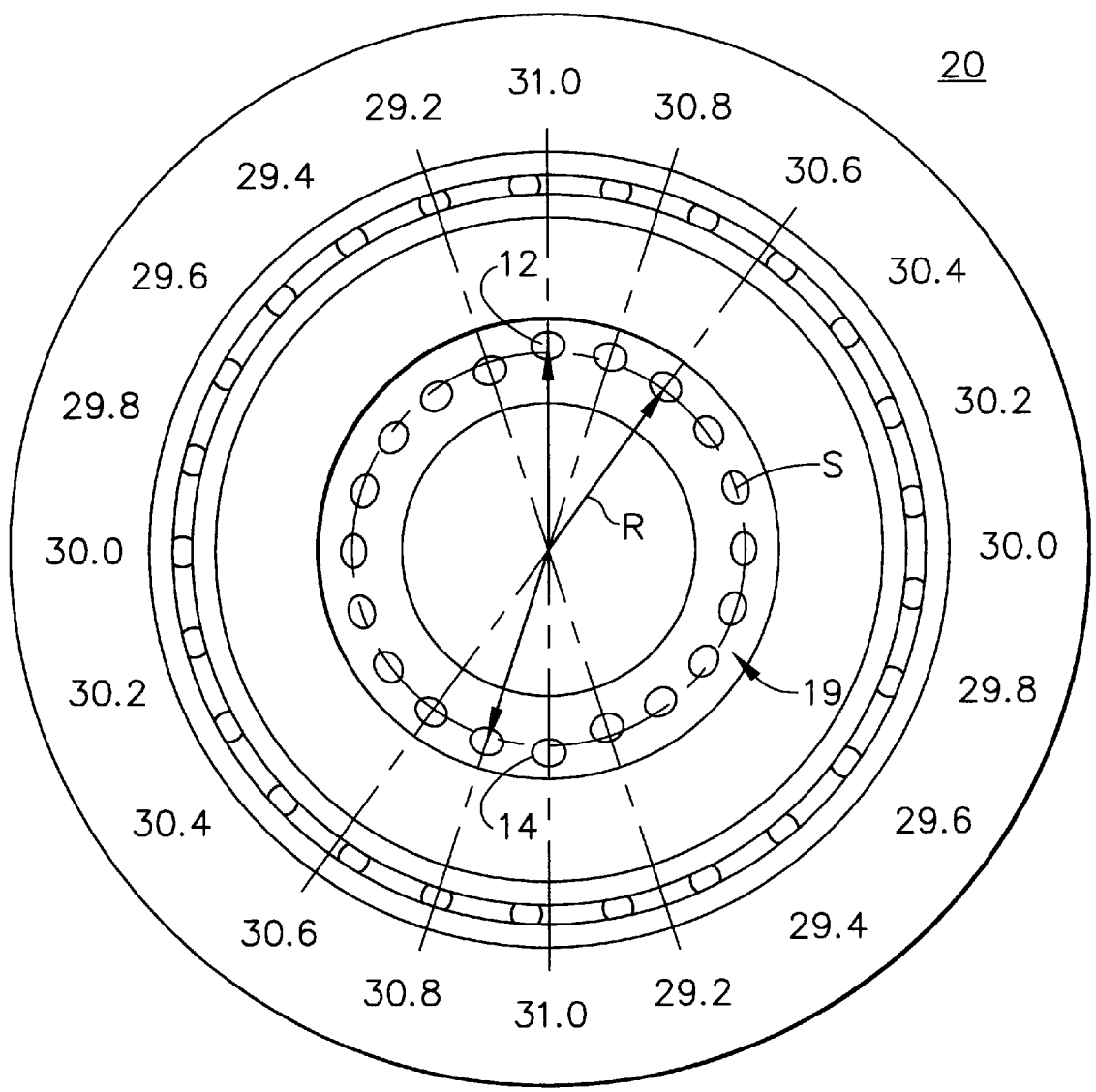
FIG. 4 is an elevated illustrative view through 4—4 of the rotatable head and transducer array and fixture in FIG. 1.

Referring now to the drawings, there is diagrammatically illustrated in FIGS. 1, 2 and 4 an ultrasonic scanning apparatus 10 having a rotatable scanning head 20 in which a rotatable array 22 of pairs of 180 degree oppositely disposed pitch and catch transducers 12 and 14, respectively, are mounted. The pitch and catch transducers 12 and 14, respectively, of each pair are mounted 180 degree circumferentially opposite of each other around a central axis CL about which the scanning head 20 is rotatable. Axes of transmission or beam axes 15 of each pair of the transducers 12 and 14 are equiangular with respect to the central axis such that incident and reflective angles A and B respectively, typically measured between the beam axes 15 and the central axis CL, are equal. The incident and reflective angles A and B respectively of the beam axes 15 of different pairs of transducers 12 and 14 are different from other pairs of transducers. Preferably, adjacent pairs have incrementally different incident and reflective angles (i.e. 0.2 degrees) with respect to the central axis. The pairs of pitch and catch transducers 12 and 14, respectively, are rotatable so that they can be positioned to interrogate a surface such as a laser shock peened surface 2 of a laser shock peened region 4 of an object, particularly a hard metallic object such as a leading edge LE of a fan blade 8.

Figure 3:
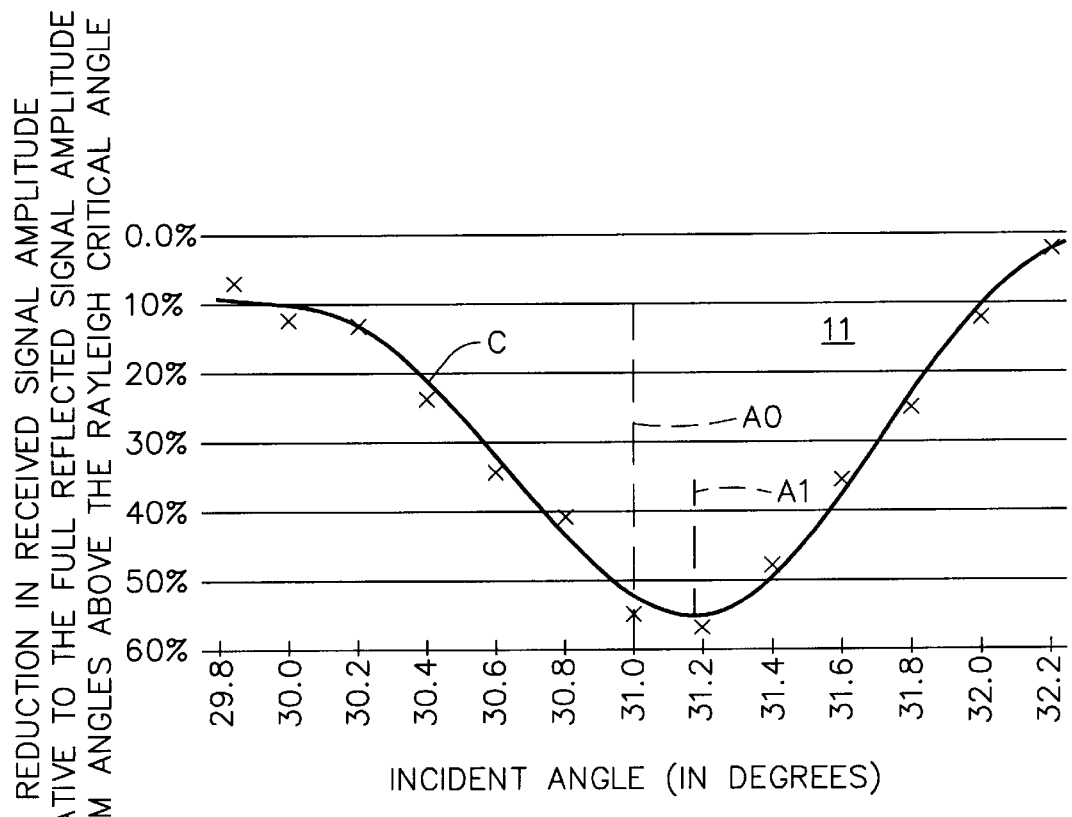
FIG. 3 is a diagram illustrating fitting a polynomial to a low amplitude portion of data representing an intensity versus incident angle profile in accordance with one method of the present invention.

It is well known in the art to adjust a single pair of pitch and catch transducers to determine an actual critical angle A', as illustrated in FIG. 3, at a point P of a metal surface. The present invention provides an apparatus and method to allow faster more cost effective measuring and using an effective critical angle A1 to determine processed material properties for process validation.

A positioning apparatus generally indicated at 9A, many types of which are well known in the art such as the one disclosed in U.S. Pat. No. 4,817,016, may be used to translate, orient, and tilt the head 20 in an x, y and z orthogonal co-ordinate system so that central axis CL may be positioned substantially normal to the surface at point P. The pitch and catch ultrasonic transducers 12 and 14, respectively, in each pair are oppositely disposed about and equally angled with respect to a centerline which coincides with the central axis CL of the array. All the transducers are positioned to transmit and/or receive the incident and reflective ultrasonic waves 16 and 18, respectively, along beam axes 15 at the same point P on the central axis CL which is to be held normal to the laser shock peened surface 2 at the point P.

The beam axes 15 of each of the pitch and catch ultrasonic transducers 12 and 14, respectively, in each pair of transducers, are equally angled with respect to the central axis CL of rotatable head 20. Each pair of the opposing transducers are preferably fixed in the rotatable scanning head 20 during the scanning and are shown (but not required to be) located along a dual spiral S where the spirals are mirror images on either side of the rotatable scanning head.

The spirals are along a fixed radius R spherical surface whose center of curvature coincides with the center of the incident beams footprint on the surface under examination which of course coincides with the point P. Each pair of transducers are fixed at a slightly different incident angle relative to the surface normal, and are rotated into position for data acquisition along a specific direction on the surface. The direction along the surface can be along the x, y and z coordinates.

FIG. 3 illustrates the rotatable scanning head 20 using a Geneva Drive 30 which may be powered by motor 9 to rotate the head about the central axis CL. The rotatable scanning head 20 includes an angular positional feedback means 31 which would have signal transmission means for coupling of the transmitted and received signals from the transducers and transmitting them out of the rotatable scanning head 20 such as through slip rings 32. The feedback means 31 is preferably also used for activating and controlling the timing of the tone bursts or pulses driving the transducers. Other types of signal transmission means may also be used such as rotary transformers, rotary capacitors, and/or optical data link couplers, all well known in the field. The rotatable transducer head and slip ring assembly illustrated herein has a hollow center 34 for visual access to the common beam impingement point P on the surface. This allows optical access to the center at point P of the incident beams footprint on the surface under examination to align the beams from the transducers such that they all impinge on the same point P on the surface and to allow some means of measuring the angular tilt error in the rotary axis or central axis CL of the system relative to the surface normal and to adjust or correct such an angular misalignment.

As the Geneva Drive rotates at a constant angular velocity, the angular velocity of the rotatable scanning head 20 cycles from zero at the data acquisition positions (which are mechanically fixed by the geometry of the drive) to a maximum at the mid point between acquisitions. At high rotational rates, these cyclic variations in angular velocity can cause considerable vibration if inertial unbalancing effects are not countered. One inertial balancing means which may be used to counter these is a counter-rotating annular collar 36 encircling the rotary transducer head. The collar has an angular inertia roughly equal to that of the rotating transducer head about their common axis of rotation which is the central axis. The collar is preferably driven by the Geneva Drive that rotates the transducer head, or it may be indirectly driven from the rotating transducer head through an idler gear (not shown). In either case, as the transducer head accelerates in one direction the inertial balancing collar accelerates in the opposite direction, thus, balancing the reaction and minimizing vibration.

The ultrasonic scanning method of the present invention is particularly useful for validation in a production environment for maintaining quality control of a laser shock peening process where time is of the essence. The incident and reflective angles A and B at which the surface is scanned are preferably predetermined and ultrasonic beam transmission and reception are simultaneously done at small predetermined intervals such as 0.2 degrees about a predetermined critical angle A0 which is illustrated as 31 degrees in FIG. 3. The received signals are converted to an intensity value and may be expressed as a % in reduction of maximum intensity as illustrated in FIG. 3 where these intensity values are profiled as a function of incidence angle at the various starting, stopping, and interval incident angles. A null angle profile 11 of intensity data is illustrated as intensity data points X in FIG. 3.

Next, a preferably second order polynomial curve fit is applied to the profile 11 of intensity data X at a mid to lower or a low amplitude portion of the profile, such as between about the 20% to 60% range of the data, as illustrated by curve C in FIG. 3. The profile 11 is preferably stored in a computer for which standardized mathematical routines are available to determine a curve fit and/or a polynomial equation using methods such as at least square fit of the data. The profile 11 of intensity data X and the polynomial curve C may both be displayed on a monitor in a manner similar to that in FIG. 3. An effective critical angle A1 may be observed from the curve C or be determined by mathematical means preferably using a polynomial equation derived from the polynomial curve fit at the minimum along the curve C. The effective critical angle A1 along the laser shock peened area of the surface may be mapped for use in quality control and as a means for non-destructive testing. Note that it is important to hold the central axis normal to the surface at the point P which is to be interrogated or ultrasonically scanned.

It has been found that 10 to 15 different angles of incidence provide a good number of intensity data points X for determining the second order polynomial equation using the least squares fit of the data to the second order polynomial. This could result in a very time consuming and error prone process if the angles had to be adjusted at a great many points on a large area to be mapped for critical angles, such as a laser shock peened leading edge LE of a gas turbine engine fan blade 8 as illustrated in FIG. 1. The present invention overcomes this problem by providing the ultrasonic scanning apparatus 10 of the present invention and a method which scans an area of interest, for example the laser shock peened leading edge, one incremental angle at a time. The entire area is scanned at each of the predetermined incident and reflective angles A and B, respectively, near the predetermined critical angle A0. The fixed predetermined incident and reflective angles A and B, respectively, are incrementally changed and fixed for the next scan or pass by rotating the head until all of the transducer pairs at their respective predetermined incident and reflective angles A and B have scanned each point P on the surface 2. The head may be rotated at the end of each pass over the surface and before the next pass. This procedure is repeated for each incremental set of predetermined incident and reflective angles such that the entire area is scanned at each predetermined incremental incidence angle until the entire area has been scanned in this manner for all the predetermined incident and reflective angles A and B respectively.

Alternatively, rather than completing a scan line or area using a single fixed transducer pair, the transducer bead may also be rotated to allow the reflected beam amplitude to be measured at all incident angles of interest at each data acquisition point and from each surface wave propagation direction before moving on to the next data acquisition point. In this way, all data necessary for the determination of effective critical angles can be acquired in a single scan over the surface of interest. The transmitting ultrasonic transducers may use pulsed tone burst, or continuous signal excitation at each incident angle, while simultaneously effecting movement between the transducers and the area being scanned. Alternatively, the scanning process may stop intermittently at each point P on the surface area, the head rotated and signal amplitude measured, and the polynomial curve fit applied to determine the critical angle at the point P as described above. In this manner the critical angle may be mapped for the entire laser shock peened surface or area of interest.

Another variation on this method is to pulse the ultrasonic transducers as the area is scanned while simultaneously effecting continuous movement between the transducers and the area being scanned. The scanning pitch and receive transducers may be moved at a constant velocity with respect to the area being mapped while the transmitting transducer is pulsed at a constant rate, and each pass of the transducers at an incrementally different incident angle can be coordinated such that the same points P in the area are interrogated on each pass. If this cannot be accomplished accurately enough then interpolation on the surface coordinates of the area such as x and y can be used to assign intensity values for each incident angle at predetermined points P on the surface in the area of interest in order to assemble the intensity vs. incident angle profile of the present invention.

Additional pairs of transducers, used to interrogate the reflected beam intensity at angles outside the high resolution angular interrogation range (the 0.2 degree interval angles about the predetermined critical angle A0), may also be incorporated in this dual spiral array. These special pairs of transducers may be used to provide total reflection beam reference amplitudes. This configuration provides that if all transducers have the same effective diameter then they will have the same beam maximum (Y0) location from the face of the transducer, and hence the same beam footprint diameter and intensity at the surface under evaluation. If multiple frequency interrogation of the surface is to be conducted, the radius R of the transducer's spherical locating surface, the transducer's diameter, and the transducers primary resonant frequency, should be selected to position the location of the beams maximum energy concentration at the surface under evaluation at the highest tone burst frequency to be used (potentially a harmonic of the primary resonant frequency). All lower frequency beams will thus intersect the surface in their more spatially uniform far field regions.

For those cases where the angular change in null location is known to be small about the predetermined and effective critical angles, the angular coverage provided by these transducers may not need to be continuous. This is because, for data processing based null detection schemes, the angular location of the beam null is primarily determined by a polynomial (or similar function) fit of the beam intensity slopes on either side of the null rather than on the null itself. It is noted that if the level of attenuation (due primarily to grain size within the material) is desired, acquisition of the effective returning beam amplitude at the null should be provided (i.e., continuous angular coverage across the null region becomes more desirable).

One feature of this configuration is that the characteristics of the null or intensity profile used to determine the effective critical angle at a given point P on the surface under examination can be generated with a single rotation of the transducer and rotatable scanning head. A single rotation of the rotatable transducer head could be used to bring every incrementally angled pair of fixed incident angle transducers in the array to any number of angular orientations with respect to the surface, limited only by the directional resolution required and the time considerations of the examination. This assumes some form of angular positional feedback means to send signals to and from the rotation head to control the orientation of the transducers for data acquisition. The benefit of this angular information would be to enable an evaluation of the magnitude of anisotropy effects due to texture or directional stress fields.

In the simplest (and least efficient) form of this system, each pair of transducers could be activated individually if necessitated by excessive crosstalk between receiving transducers (particularly between adjacent receiving transducers). However, simultaneous interrogation of all directional angles, provided by the rotational position of the transducers around the rotary head, is the operational mode of choice in minimizing the data acquisition time. In the event that crosstalk is not a problem, all transmitting transducers 12 may be ganged together and driven simultaneously, preferably by a tone burst. Tone burst excitation is preferred as a more stable steady state acoustic beam may be generated by the transducer at frequencies below (or in harmonic multiples above) its primary resonant frequency. A full rotation of the transducer head is still required to measure all incident angles in all directions, i.e. different transducer pair angular orientations around the central axis CL. In the event that cross talk between adjacent receivers is a problem of limited proportion, the propagation directions could be alternated as seen in the graphic (i.e. transmitter—receiver—transmitter—receiver, etc. around the ring). Finally, the number of transmitting transducers ganged together could be limited to smaller more orthogonally oriented groups to further limit sensitivity to cross talk.

In all cases, signals from the receiving transducers are treated individually, with their own (under most circumstances gated) signal (peak, peak to peak, or RMS) level detection and logging circuitry. The resultant basic data output of this system is expected to be a series of files containing returning signal amplitude for each excitation frequency, from each incident angle transducer pair, at each desired surface wave propagation direction, and at each pixel location on the surface under examination as explained above. From these data, The Rayleigh Critical Angle and level of returning signal amplitude may be determined as a basis for the generation of maps of the various acoustic characteristics of the surfaces under examination. For instance plots of velocity with respect to direction at a specific point on the surface for evaluation of anisotropic characteristics, or plots of velocity with respect to frequency for evaluation of depth effects. In the case of LSP, these plots are in addition to the differential (before and after LSP) plots of velocity that are expected to be the primary measure of LSP based residual stress effects in a material. Velocity measurements assume temperature effects at the location of the critical angle have been removed.

The foregoing descriptive embodiments of the invention have been presented for the purpose of describing and illustrating the invention. It is not intended to be exhaustive or to limit the invention to the precise form disclosed and obviously many modifications and variations are possible in light of the above teachings. While the preferred embodiment of the invention has been described fully in order to explain its principles, it is understood that various modifications or alterations may be made to the preferred embodiment without departing from the scope of the invention as set forth in the appended claims.

What is claimed is:

1. An apparatus for ultrasonic scanning a surface, said apparatus comprising:
   a plurality of pairs of 180 degree oppositely disposed ultrasonic transducers having beam axes;
   said transducers mounted in a rotatable head having a central axis about which said head is rotatable; and
   a positioning means for positioning said transducers such that all of said beam axes intersect said central axis at a single point, said beam axes within each pair of said transducers are equiangular with respect to said central axis, and said beam axes of different pairs of transducers have incident and reflective angles respectively of said beam axes that are different from those of other pairs.

2. An apparatus as claimed in claim 1 wherein said positioning means is a fixture having a plurality of angled holes in which said transducers are disposed.

3. An apparatus as claimed in claim 2 wherein distances from said transducers to said point along said transmission axes are equal.

4. An apparatus as claimed in claim 3 further comprising transducer angles between said beam axes and said central axis wherein said transducer angles of said different pairs of transducers are predetermined and in close proximity to a predetermined angle.

5. An apparatus as claimed in claim 4 wherein said transducer angles are set at intervals of about 0.2 of a degree greater than and less than said predetermined angle.

6. An apparatus as claimed in claim 2 further comprising a translating means for effecting translational motion between head and the surface and positioning said head with respect to the surface such that said point lies substantially on the surface during ultrasonic scanning.

7. An apparatus as claimed in claim 2 further comprising a translating means for translating said head over the surface and positioning said head above the surface such that said point lies substantially on the surface during ultrasonic scanning.

8. An apparatus as claimed in claim 1 further comprising a counter-rotatable annular collar encircling said head and counter-rotating motive means to drive said collar in a circular direction counter to that of said head about said central axis when said head is rotated.

9. An apparatus as claimed in claim 8 wherein said positioning means is a fixture having a plurality of angled holes in which said transducers are disposed.

10. An apparatus as claimed in claim 9 wherein distances from said transducers to said point along said transmission axes are equal.

11. An apparatus as claimed in claim 10 further comprising transducer angles between said beam axes and said central axis wherein said transducer angles of said different pairs of transducers are predetermined and in close proximity to a predetermined angle.

12. An apparatus as claimed in claim 11 further comprising a translating means for translating said head over the surface and positioning said head above the surface such that said point lies substantially on the surface during ultrasonic scanning.

13. An apparatus as claimed in claim 12 wherein said transducer angles are set at intervals of about 0.2 of a degree greater than and less than said predetermined angle.

14. A method for determining Rayleigh wave effective critical angles at a surface of a metallic object, said method comprising the steps of:
   (a) rotating a plurality of pairs of 180 degree oppositely disposed ultrasonic transducers mounted in a rotatable head around a central axis wherein the transducers have beam axes set at fixed angles with respect to the central axis such that the fixed angles of each pair of transducers are equiangular with respect to said central axis, and the fixed angles of different pairs of transducers are different with respect to the central axis;
   (b) directing incident beams of ultrasonic waves onto at least one point of the surface at a plurality of incident angles along the beam axes of the different pairs of transducers at the different fixed angles;

(c) simultaneously measuring intensity of a combination of corresponding directly reflected and re-radiated beams from the incident beams; and (d) determining the effective critical angle from intensity data gathered in step (c) wherein the effective critical angle is a determined angle of incidence at which the energy of the reflected beam is indicated to be a substantially minimum amount based on the intensity data at the point of the surface.

15. A method as claimed in claim 14 wherein said determining the effective critical angle in step (d) further comprises:

(e) generating a null angle profile of data indicating intensity versus corresponding incident angles from measured intensities in step (c);

(f) determining an intensity curve by applying a curve fit to a low intensity portion of the null angle profile; and (g) determining the effective critical angle by determining a substantially minimum point on the curve, the effective critical angle being equal to a determined angle of incidence at which the energy of the reflected beam is the substantially minimum point on the curve.

16. A method as claimed in claim 15 wherein said curve fit is a polynomial fit.

17. A method as claimed in claim 16 wherein said polynomial curve fit is a second order polynomial fit.

18. A method for mapping Rayleigh wave effective critical angles on a surface area of a metallic object, said method comprising the steps of:

(a) scanning incident beams of ultrasonic waves at a plurality of points on the area at a plurality of incident angles by rotating a plurality of pairs of 180 degree oppositely disposed ultrasonic transducers mounted in a rotatable head around a central axis wherein the transducers have beam axes set at fixed angles with respect to the central axis such that the fixed angles of each pair of transducers are equiangular with respect to said central axis, the fixed angles of different pairs of transducers are different with respect to the central axis, and the fixed angles are in close proximity to at least one predetermined angle;

(b) simultaneously measuring intensity of a combination of corresponding directly reflected and re-radiated beams at a plurality of corresponding reflected angles equal in magnitude to said incident angles with respect to a line normal to the surface;

(c) generating a plurality of null angle profiles of data indicating intensity versus corresponding incident angles from measured intensities in step (b) at the plurality of points on the area;

(d) determining intensity curves for said points by applying curve fits to low intensity portions of the null angle profiles at their respective points on the surface; and (e) determining the effective critical angles by determining substantially minimum points on the curves, said effective critical angles being equal to determined angles of incidence at which the energy of the reflected beams are the substantially minimum points on the respective curves.

19. A method as claimed in claim 18 wherein said curve fits are polynomial fits.

20. A method as claimed in claim 19 wherein said polynomial curve fits are second order polynomial fits.

21. A method as claimed in claim 20 wherein the scanning comprises a plurality of passes of the rotatable head with the transducers held at a fixed angular orientation around the central axis during each pass, pitch and catch transducers of the plurality of transducers are the positioned to the same angular orientation during each pass, and head is rotated between passes such that different ones of the plurality of transducers are used as the pitch and catch transducers in each of the passes.

22. A method as claimed in claim 21 wherein the pitch and catch transducers are operated in bursts over the points in the area during each pass.

23. A method as claimed in claim 19 wherein the scanning comprises a single pass of the rotatable head with the head stopping at each of the points, at each of the points the head is rotated and step (b) is performed.

* * * * *